United States Patent
Oostman, Jr.

(10) Patent No.: US 8,876,839 B2
(45) Date of Patent: Nov. 4, 2014

(54) FOLLICULA UNIT REMOVAL TOOL WITH PIVOTING RETENTION MEMBER AND METHOD OF ITS USE

(71) Applicant: Restoration Robotics, Inc., San Jose, CA (US)

(72) Inventor: Clifford A. Oostman, Jr., Hansville, WA (US)

(73) Assignee: Restoration Robotics, Inc., San Jose, CA (US)

( * ) Notice: Subject to any disclaimer, the term of this patent is extended or adjusted under 35 U.S.C. 154(b) by 131 days.

(21) Appl. No.: 13/628,827

(22) Filed: Sep. 27, 2012

(65) Prior Publication Data

US 2013/0023902 A1  Jan. 24, 2013

Related U.S. Application Data

(62) Division of application No. 12/752,889, filed on Apr. 1, 2010, now Pat. No. 8,298,246.

(51) Int. Cl.
| | |
|---|---|
| *A61B 17/3205* | (2006.01) |
| *A61B 17/30* | (2006.01) |
| *A61B 17/00* | (2006.01) |
| *A61B 17/32* | (2006.01) |

(52) U.S. Cl.
CPC .......... *A61B 17/32053* (2013.01); *A61B 17/30* (2013.01); *A61B 2017/00752* (2013.01); *A61B 2017/320064* (2013.01)
USPC .......................................... 606/133; 606/205

(58) Field of Classification Search
CPC ............. A61B 17/30; A61B 17/32053; A61B 2017/00752; A61B 19/2203
USPC ......... 606/130, 133, 167, 170, 171, 205–211; 600/562–572
See application file for complete search history.

(56) References Cited

U.S. PATENT DOCUMENTS

| | | | |
|---|---|---|---|
| 3,561,429 | A | 2/1971 | Jewett |
| 3,605,721 | A | 9/1971 | Hallac |
| 3,998,230 | A | 12/1976 | Miller |
| 4,160,453 | A | 7/1979 | Miller |

(Continued)

FOREIGN PATENT DOCUMENTS

| | | |
|---|---|---|
| EP | 0966920 | 12/1999 |
| EP | 1293167 | 3/2003 |

(Continued)

OTHER PUBLICATIONS

English Translation of Office Action mailed Nov. 27, 2013 in connection with commonly assigned, Korean Patent Application No. 10-2012-7025634. Restoration Robotics, Inc. (4 pages).

(Continued)

*Primary Examiner* — Kathleen Holwerda
(74) *Attorney, Agent, or Firm* — Lena I Vinitskaya; Sharon Upham

(57) ABSTRACT

Tools and methods are provided for removing follicular units from a body surface while improving retention of the follicular units in the removal tool. The removal tool is configured to accommodate a retention member. The retention member may comprise pivotally movable elements which retain the follicular unit in the removal tool. The described tools and methods are especially useful for harvesting follicular units from a body surface in a hair transplantation process.

25 Claims, 4 Drawing Sheets

(56) References Cited

U.S. PATENT DOCUMENTS

| | | | |
|---|---|---|---|
| 4,243,040 A | 1/1981 | Beecher | |
| 4,393,872 A | 7/1983 | Reznik et al. | |
| 4,427,014 A | 1/1984 | Bel et al. | |
| 4,640,296 A | 2/1987 | Snepp-Pesch et al. | |
| 4,708,147 A | 11/1987 | Haaga | |
| 4,716,901 A | 1/1988 | Jackson et al. | |
| 4,781,202 A | 11/1988 | Janese | |
| 4,785,826 A | 11/1988 | Ward | |
| 4,946,440 A | 8/1990 | Hall | |
| 4,971,067 A * | 11/1990 | Bolduc et al. | 600/564 |
| 5,036,860 A | 8/1991 | Leigh et al. | |
| 5,341,816 A | 8/1994 | Allen | |
| 5,423,330 A | 6/1995 | Lee | |
| 5,462,062 A | 10/1995 | Rubinstein et al. | |
| 5,480,388 A | 1/1996 | Zadini et al. | |
| 5,573,008 A | 11/1996 | Robinson et al. | |
| 5,584,841 A | 12/1996 | Rassman | |
| 5,788,651 A | 8/1998 | Weilandt | |
| 5,794,626 A | 8/1998 | Kieturakis | |
| 5,817,120 A | 10/1998 | Rassman | |
| 5,885,226 A | 3/1999 | Rubinstein et al. | |
| 5,893,853 A | 4/1999 | Arnold | |
| 5,910,121 A | 6/1999 | Paolo et al. | |
| 6,015,391 A | 1/2000 | Rishton et al. | |
| 6,080,175 A | 6/2000 | Hogendijk | |
| 6,086,543 A | 7/2000 | Anderson et al. | |
| 6,110,127 A | 8/2000 | Suzuki | |
| 6,142,955 A | 11/2000 | Farascioni et al. | |
| 6,273,861 B1 | 8/2001 | Bates et al. | |
| 6,315,737 B1 | 11/2001 | Skinner | |
| 6,395,002 B1 | 5/2002 | Ellman et al. | |
| 6,416,484 B1 | 7/2002 | Miller et al. | |
| 6,461,369 B1 | 10/2002 | Kim | |
| 6,464,711 B1 | 10/2002 | Emans et al. | |
| 6,471,709 B1 | 10/2002 | Fawzi et al. | |
| 6,488,636 B2 | 12/2002 | Bryan et al. | |
| 6,554,779 B2 | 4/2003 | Viola et al. | |
| 6,572,625 B1 | 6/2003 | Rassman | |
| 6,770,026 B2 | 8/2004 | Kan et al. | |
| 6,875,220 B2 | 4/2005 | Du et al. | |
| 6,918,880 B2 | 7/2005 | Brookner et al. | |
| 6,939,318 B2 | 9/2005 | Stenzel | |
| 7,014,614 B2 | 3/2006 | Casula | |
| 7,147,656 B2 | 12/2006 | Andreas et al. | |
| 7,201,722 B2 | 4/2007 | Krueger | |
| 7,261,721 B2 | 8/2007 | Feller | |
| 7,517,321 B2 | 4/2009 | McCullough et al. | |
| 7,621,933 B2 | 11/2009 | Bodduluri et al. | |
| 7,621,934 B2 | 11/2009 | Bodduluri et al. | |
| 7,635,340 B2 | 12/2009 | Vetter et al. | |
| 7,762,959 B2 | 7/2010 | Bilsbury | |
| 7,775,989 B2 | 8/2010 | Nakao | |
| 2002/0151821 A1 | 10/2002 | Castellacci | |
| 2003/0097079 A1 | 5/2003 | Garcia | |
| 2003/0097144 A1 | 5/2003 | Lee | |
| 2004/0092924 A1 | 5/2004 | Vasa | |
| 2004/0220589 A1 | 11/2004 | Feller | |
| 2005/0043718 A1 | 2/2005 | Madhani et al. | |
| 2005/0085838 A1 | 4/2005 | Thompson et al. | |
| 2005/0131313 A1 | 6/2005 | Mikulka et al. | |
| 2005/0267506 A1 | 12/2005 | Harris | |
| 2006/0161179 A1 | 7/2006 | Kachenmeister | |
| 2006/0173377 A1 | 8/2006 | McCullough et al. | |
| 2007/0123800 A1 | 5/2007 | Nishtala et al. | |
| 2007/0142743 A1 | 6/2007 | Provencher et al. | |
| 2007/0149985 A1 | 6/2007 | Cole | |
| 2007/0213634 A1 | 9/2007 | Teague | |
| 2007/0213741 A1 | 9/2007 | Cole | |
| 2008/0033455 A1 | 2/2008 | Rassman et al. | |
| 2008/0045858 A1 | 2/2008 | Tessitore et al. | |
| 2008/0154150 A1 | 6/2008 | Goldenberg | |
| 2008/0154296 A1 | 6/2008 | Taylor et al. | |
| 2008/0234602 A1 * | 9/2008 | Oostman et al. | 600/564 |
| 2009/0227895 A1 | 9/2009 | Goldenberg | |
| 2009/0240261 A1 | 9/2009 | Drews et al. | |
| 2010/0082042 A1 | 4/2010 | Drews et al. | |

FOREIGN PATENT DOCUMENTS

| | | |
|---|---|---|
| WO | 97/06749 | 2/1997 |
| WO | 0207602 | 1/2002 |
| WO | 02065919 | 8/2002 |
| WO | 2005/109799 | 11/2005 |
| WO | 2006/081556 | 8/2006 |
| WO | 2008027829 | 3/2008 |
| WO | WO 2008/115526 | 9/2008 |
| WO | 2009017445 | 2/2009 |

OTHER PUBLICATIONS

English Translation of Office Action mailed Nov. 5, 2013 in connection with commonly assigned Japanese Patent Application No. 2013-502680. Restoration Robotics, Inc. (4 pages).

Supplemental Search and Written Opinion in connection with commonly assigned European Patent Application No. 11763269.5 Restoration Robotics, Inc. mailed Nov. 29, 2013 (6 pages).

PCT International Search Report and Written Opinion for commonly assigned PCT/US2011/030022, In the name of Restoration Robotics, Inc. Forms PCT/ISA/220, PCT/ISA/210 and PCT/ISA/237, mailed Dec. 7, 2011. [12 pages].

Non-Final Office Action dated Aug. 27, 2012, in relation to commonly assigned U.S. Appl. No. 12/558,102 (17 pages).

Harris, James A. "New Methodology and Instrumentation for Follicular Unit Extraction: Lower Follicle Transection Rates and Expanded Patient Candidacy". Department of Otolaryngology/Head and Neck Surgery, Univ. of Colorado Health Sciences Center, Denver, Colorado. Copyright 2006 by the American Society of Dermatologic Surgery, Inc. Published by BC Decker, Inc., Dermatologic Surgery, vol. 32.

Robert M Bernstein, MD; William R Rassman, MD. "New Instrumentation for Three-Step Follicular Unit Extraction". Hair Transplant Forum International, vol. 16, No. 1, Jan. /Feb. 2006.

English Translation of Office Action mailed Jun. 17, 2014, in connection with commonly assigned Chinese Patent Application No. 201180016432.6. Restoration Robotics, Inc. (3 pages).

English Translation of Office Action mailed Jun. 27, 2014, in connection with commonly assigned Korean Patent Application No. 10-2012-7025634. Restoration Robotics, Inc. (2 pages).

* cited by examiner

FOLLICULA UNIT REMOVAL TOOL WITH PIVOTING RETENTION MEMBER AND METHOD OF ITS USE

FIELD OF THE INVENTION

This application is a division of co-pending U.S. patent application Ser. No. 12/752,889, filed Apr. 1, 2010, and entitled FOLLICULAR UNIT REMOVAL TOOL WITH PIVOTING RETENTION MEMBER.

FIELD OF THE INVENTION

The present invention relates generally to tools and methods used for the harvesting of follicular units, in particular, tools and methods used in conjunction with hair transplantation procedures.

BACKGROUND OF THE INVENTION

Hair transplantation procedures are well-known, and typically involve harvesting donor hair grafts from the "donor areas," for example, side and back fringe areas of the patient's scalp, and implanting them in a bald area ("recipient area"). Historically, the harvested hair grafts were relatively large (3-5 mm), although more recently the donor grafts may be single follicular units, which are naturally occurring aggregates of 1-3 (and much less commonly, 4-5) closely spaced hair follicles ("the FUs") that are distributed over the surface of the body. In one well-known process, a linear portion of the scalp is removed from a donor area by dissection, using a scalpel to cut down into the fatty subcutaneous tissue. The strip is then dissected (under a microscope) into the component follicular units, which are then implanted into a recipient area in respective puncture incisions made by a needle or razor blade. Forceps are typically used to grasp and place the follicular unit grafts into the needle puncture locations, although other instruments and methods are known for doing so:

For instance, U.S. Pat. No. 7,172,604 (Cole) discloses an instrument for the extraction of individual follicular units. U.S. Patent Publication 20050267506 (Harris) discloses a method and apparatus for the extraction of follicular units by first scoring the outer skin layers with a sharp punch, and then inserting a blunt punch into the incision to separate the hair transection. Another U.S. Pat. No. 6,585,746 (Gildenberg) discloses a hair transplantation system utilizing a robotic system, including a robotic arm and a hair follicle end effector associated with the robotic arm that could be used to harvest hair follicles from the donor area.

Despite certain advances in improving the tools for harvesting of follicular units, there remains a need for a more efficient harvesting tool that increases the yield of usable harvested specimens, improves retention of the harvested units in the removal tool and the quality of the obtained specimens.

SUMMARY OF THE INVENTION

According to one aspect of the disclosure, a follicular unit removal tool is provided. The tool may comprise an elongated body having a lumen and a distal end with a tip configured to penetrate a body surface, the lumen of the elongated body being configured and having a capacity to receive one or more follicular units. The tool also comprises a retention member configured to be accommodated by the elongated body and to be pivotally movable from a retracted position to a retention position, such that in the retention position at least a portion of the retention member projects into the lumen of the elongated body. Further, the tool comprises an actuator configured to cause the retention member to pivot from the retraction to the retention position and/or from the retention to the retraction position, wherein the elongated body is configured to accommodate the retention member without compromising the capacity of the lumen available to receive the one or more follicular units. The removal tool may be manually operated, it could be a hand-held device, or it could be configured to be operatively connected to a robotic arm and it could be operated using a substantially automated process.

In some embodiments, the elongated body is further configured to accommodate the retention member without substantially increasing a size of a portion of the elongated body that enters a body surface when in use. In some embodiments, the retention member comprises at least two pivotally movable elements, and wherein an axial movement of the actuator causes the at least two pivotally movable elements to pivot from the retracted to the retention position and converge. In further embodiments, the elongated body may comprise a depression which provides a pivotal axis for the retention member.

The retention member may be configured to define a portion of the elongated body. The retention member may further comprise a protuberance, and the actuator may cause the protuberance to be urged in a radial direction and the retention member to pivot. In some embodiments, the portion of the retention member that projects into the lumen may comprise gripping features to grip the follicular unit.

According to another aspect, the method for retaining a follicular unit in the follicular unit removal or harvesting tool is provided. The method comprises inserting a follicular unit removal tool comprising an elongated body and a retention member into a body surface, such that a distal end of the elongated body penetrates the body surface and receives a follicular unit in a lumen of the elongated body. The method further comprises pivoting the retention member between a retracted position and a retention position such that in the retention position at least a portion of the retention member projects into the lumen of the elongated body, and in the retracted position the retention member defines a portion of the lumen thereof. The method may be substantially automated, for example, performed using a robotic system. Alternatively, the method may be performed using a hand-held device for follicular unit removal.

In some embodiments of the method, pivoting the retention member comprises moving an actuator over at least a portion of the elongated body. In other embodiments, the method also comprises connecting the follicular unit removal tool to a source of fluid or gas to assist movement of the follicular unit in the elongated body in a proximal direction.

In some embodiments of the method, the retention member may comprise a plurality of pivotable elements, and movement of the actuator causes the plurality of pivotable members to move from the retracted position to the retention position and converge.

Other and further objects and advantages of the invention will become apparent from the following detailed description when read in view of the accompanying figures.

BRIEF DESCRIPTION OF THE DRAWINGS

Features and advantages of the embodiments described will become appreciated as the same become better understood with reference to the specification, claims, and appended drawings wherein:

DETAILED DESCRIPTION OF THE PREFERRED EMBODIMENTS

Figure 1A:
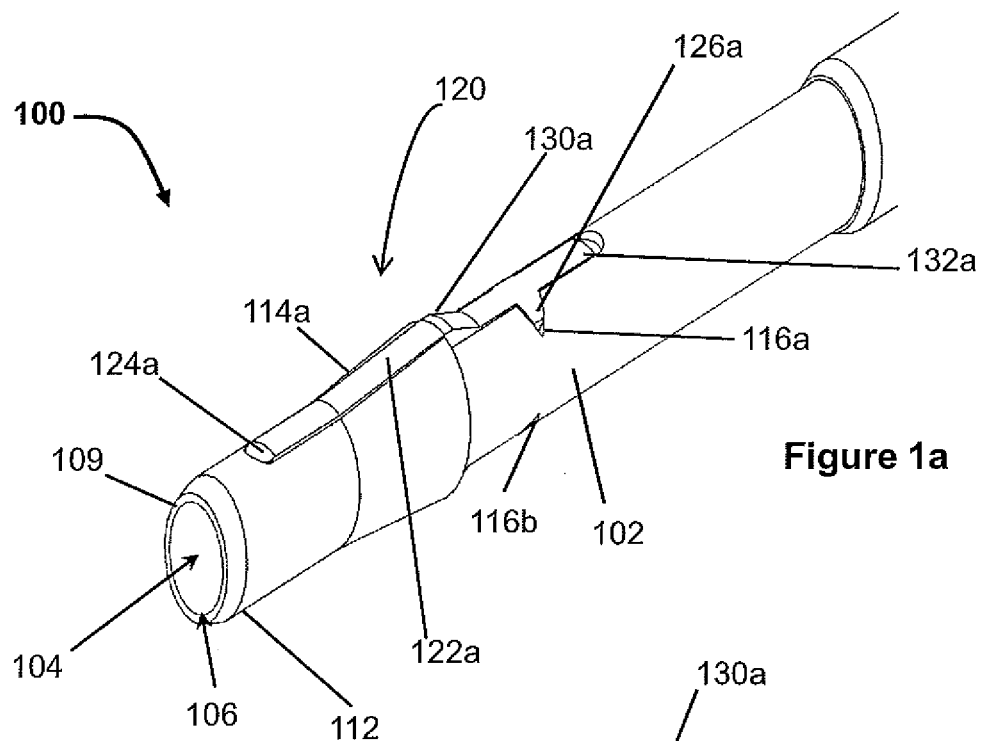
FIG. 1a is a perspective view of an embodiment of a follicular unit removal tool of the present application, in its retracted position.

In the following Detailed Description, reference is made to the accompanying drawings that show by way of illustration some examples of embodiments in which the invention may be practiced. In this regard, directional terminology, such as "top," "bottom," "inner", "outer", "distal," "proximal," etc., is used with reference to the orientation of the Figure(s) being described. Because components or embodiments described herein can be positioned in a number of different orientations, the directional terminology is used for purposes of illustration and is in no way limiting. It is to be understood that other embodiments may be utilized and structural or logical changes may be made without departing from the scope of the present application. The following description, therefore, is not to be taken in a limiting sense, and the scope of the inventions described is defined by the appended claims.

The devices and methods of the current application are useful in manual procedures and systems, as well as in automated procedures and system. Some of the automated systems described herein may also be robotically-assisted or computer/software/machine-instruction instruction controlled. The tools of the current application can also be used with the robotically-assisted systems and procedures and they could be configured for use with those robotic systems, for example, as described in the commonly-assigned U.S. Patent Publication No. 2007/0106306, the disclosure of which is incorporated herein by reference.

The term "tool", "follicular unit removal tool" or "harvesting cannula" as used herein refers to any number of tools or end effectors that are capable of removing or harvesting follicular units ("FUs") from a body surface. A body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The distal end of removal tools (for example, punches, coring devices, cutting and/or trimming devices, needles), is typically configured to cut and extract the tissue (e.g., hair follicle).

Various embodiments of follicular unit harvesting cannulas (or tools) described herein may be employed in harvesting systems, whether such systems are fully-automated (e.g., robotically controlled), semi-automated, or manually controlled, for example, using hand-held devices. It will be appreciated by those skilled in the art that each harvesting cannula design may have certain benefits (e.g., superior retraction and retention of follicular units, less trauma to the surrounding skin and tissue), or drawbacks (e.g., complex design and/or operation, higher manufacturing costs, increased trauma), relative to the other embodiments. Thus, selection of a particular harvesting cannula distal end design will depend on the particular performance criteria sought to be achieved.

As mentioned above, the present application is particularly useful in hair harvesting, to provide devices and methods for harvesting hair grafts, e.g., follicular units (FUs). As such, the term follicular units (or FUs) will be used herein simply as an example for purposes of describing some embodiments with the understanding that it represents hair grafts, follicles, or follicular unit(s).

According to an aspect of the present application, there is provided a follicular unit removal or harvesting tool, with a retention member. Removal or harvesting tools generally have a tubular elongated body with a cylindrical profile and a hollow lumen therethrough, although these tools do not have to be tubular and the profile may be other than cylindrical (e.g., curved and not straight, or other than circular in section). Furthermore, although a particularly useful follicular unit removal tool includes a hollow lumen that extends through the elongated body from one end to another, it is also possible that the lumen only extends part way along the length of the elongated body. More particularly, suction or vacuum may be used with the follicular unit removal tools described herein, and suction may be created through a lumen that extends the entire length of the elongated body, or in a lumen that only extends part of the way along the body. The retention members described herein may be positioned not only at the distal portion of the tool, but also in various locations along the body of the tool, for example, a short distance from the distal end of the tool, or midway along the body of the tool, depending upon the configuration of the tool and its intended purpose. The terms "coupled," or "attached," or "connected," or "mounted" as used herein, may mean directly or indirectly coupled, attached, integrated, or mounted through one or more intervening components.

A "retention member" as used herein refers to a structure, or a mechanism, or a number of structures and/or mechanisms that partially or fully retain a follicular unit in a lumen of various follicular removal tools. The retention member may translate into or across the lumen, or radially constrict the lumen in a circumferential manner, for example, simply closing tightly about a follicular unit, located in the lumen to improve its retention and removal without damaging it. The retention members described herein may be made of a variety of biocompatible materials, such as polypropylene, polyester, polyurethane, Teflon, Nitinol, stainless steel, etc. The configuration of the retention members may be solid, braided, filamentous, etc., and should not be considered limited to any one particular embodiment.

Figure 1B:
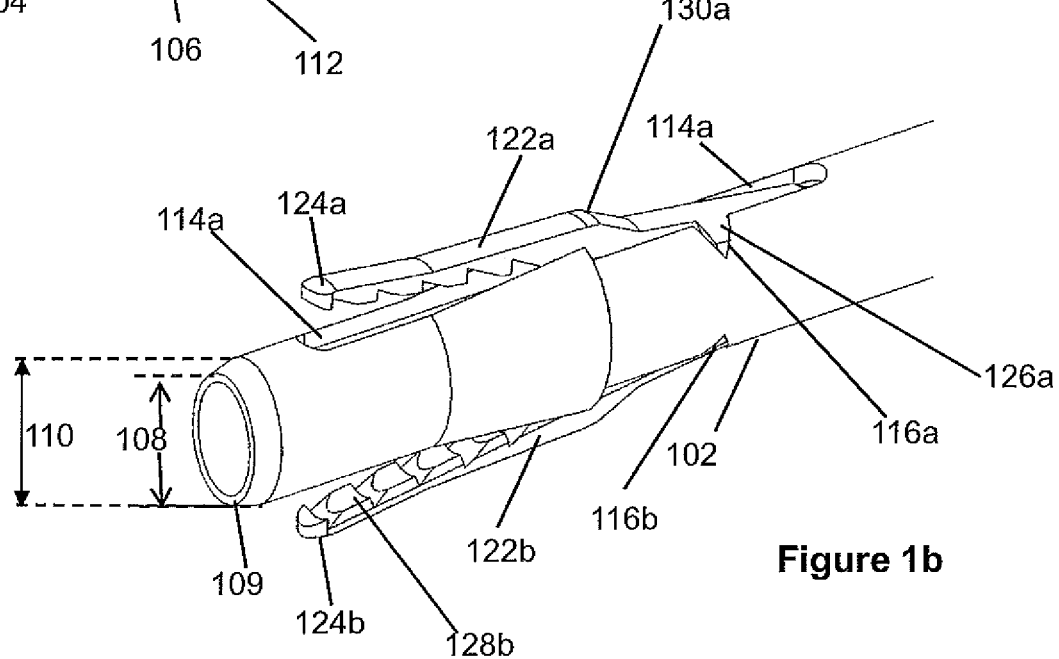
FIG. 1b is a perspective view of the follicular unit removal tool of FIG. 1a, in a position to aid in the description of its structure.
Figure 2:
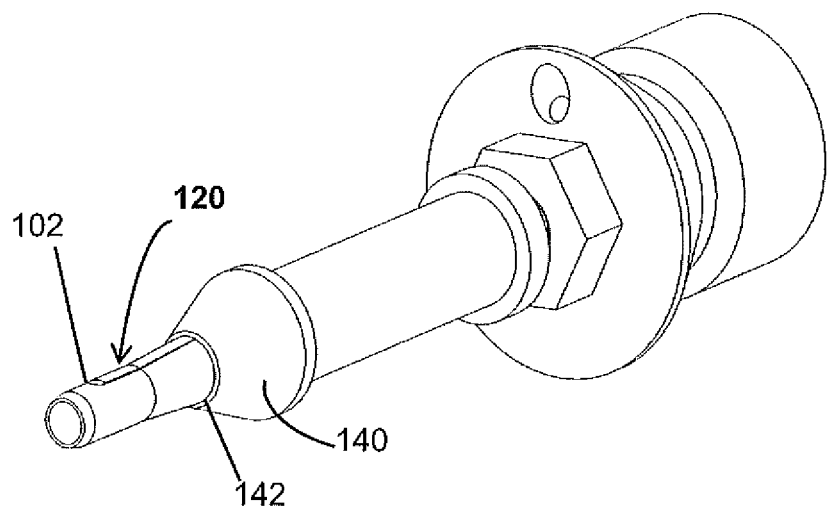
FIG. 2 is an example of a perspective view of a follicular unit removal tool incorporated into a system with an actuator.

FIGS. 1a and 1b illustrate an example of a follicular unit removal tool according to an embodiment of the present application, with some features shown in a somewhat exaggerated configuration in order to aid in the description thereof. The tool 100 comprises an elongated body 102 which is illustrated as generally tubular with a hollow interior forming the lumen 104 thereof, and a distal tip having an opening 106, the tip is configured to penetrate a body surface. The elongated body 102 has both an internal diameter 108 and an external diameter 110, either of which may comprise in some embodiments predetermined dimensions. The internal and external diameters 108 and 110 define a wall 109 of the elongated body 102. The tool 100 may be used to remove or harvest one or a plurality of follicular units, and will be correspondingly sized, having the capacity to receive the follicular unit or units of interest. For example, the follicular unit removal tool 100 may comprise a lumen 104 with a diameter of between about 0.5 and 1.5 mm, having the capacity to receive one or more follicular units. Only a distal portion of the tool 100 is shown, the length and proximal termination varying dependent on how and the type of system with which it is to be used. The tool 100 may have a length of between about 4 to 25 mm depending on the application. As indicated earlier, in this particular configuration illustrated the tool has a generally cylindrical profile but reduces to a smaller profile at the distal end 112 thereof, tapering towards the distal tip as shown to more easily facilitate penetration of the body surface (not shown). The elongated body 102, in the example shown, has two additional side openings, only one 114a which can be clearly seen in FIG. 1b. The purpose of these openings will be discussed below.

In one aspect of the present application, a tool 100 is provided which is configured to accommodate a retention member 120, in such a way that the capacity of the lumen 104 available to receive the follicular unit is not compromised or sacrificed by the inclusion of the retention member 120. In another aspect of the present application, for example, an overall cross-sectional dimensions, or size, or the cross-sectional profile of the follicular unit removal tool as it penetrates the body surface with the retention member 120, is not substantially different from the corresponding size, dimensions, or profile of the follicular unit removal tool without such a retention member 120.

The retention member 120 in the configurations illustrated in FIGS. 1-4 comprises, as an example, two pivotally movable elements 122a and 122b. FIG. 1b shows the pivotally movable elements 122a and 122b pivoted such that the retention member 120 is in a much exaggerated open position, with the distal ends 124a and 124b of the pivotally movable elements 122a and 122b shown to be pivoted substantially away from the elongated body 102. However, the distal ends 124a and 124b are movable such that they are able to pivot through the side openings 114a and 114b (not shown) of the elongated body 102 and into the lumen 104 of the elongated body 102. The axes 126a and 126b about which the distal ends 124a and 124b pivot, may be disposed in a depression, such as grooves 116a and 116b of the elongated body 102. The grooves 116a, 116b thus providing fulcrums about which the pivotally movable elements 122a and 122b are able to pivot. Although in the example shown in FIG. 1b, the fulcrum structure provided is in the form of grooves or depressions 116a and 116b disposed in the outwardly facing surfaces of the elongated body 102, it will be appreciated that the fulcrums can be provided by other such suitable structures or features. For example, the fulcrum may be provided by a shaft in a bearing or a hole. Alternatively, one or more pivotally movable elements may be attached to a flexible member (e.g., spring) to provide a flexure in place of a fulcrum.

The pivotally movable elements 122a and 122b are configured such that when in use, in the retracted position, they may form a part of the elongated body 102, filling in for example the side openings 114a and 114b. In other words, the surfaces of the movable elements 122a and 122b that face the lumen 104 of the elongated body 102 (see surface 128b shown in FIG. 1b) may be substantially aligned with and serve to define portions of the inner surface of the wall 109 of the elongated body 102, thus defining a portion of the lumen of the elongated body. Also, in the retracted position, an outer surface of the retention member may lay substantially along an outer surface of the elongated body 102. For example, the retention member may be configured to be at least partially disposed in the wall 109 of the elongated body 102. Therefore, in the retracted position, the pivotally movable elements 122a and 122b are preferably substantially flush with the lumen wall of the elongated body 102 (see FIG. 1a). By configuring the pivotally movable elements 122a and 122b appropriately, the cross-sectional profile (or the footprint) made by the elongated body 102 as it penetrates the body surface, will therefore be substantially the same as the cross-sectional profile (or the footprint) made by an elongated body that does not incorporate such a retention member.

The pivotally movable elements 122a and 122b may have at least a portion of their inwardly facing surfaces 128a and 128b respectively, adapted to minimize the trauma experienced by the follicular unit. Such adaptations including, for example, modification to the shape or finish, and/or the application of a coating to the inwardly facing surfaces 128a and 128b of the pivotally movable elements 122a and 122b. Adaptations may include, but are not limited to, some features that comprise non-knife-like, blunt or rounded edges, jagged edges, tapers or other such gradual transitions, crown-like shaping, roughened or ridged finishes, that are collectively referred to as gripping features. These non-traumatic inwardly facing surfaces may be incorporated into any of the embodiments of the retention members.

The pivotably movable members 122a, 122b may be caused to pivot using an actuator 140. In some embodiments, the actuator may move distally/proximally substantially parallel to the longitudinal axis of the elongated body 102, and control movement of the pivotably movable members 122a and 122b from the retracted to the retention position, in and out of the respective openings 114a and 114b. For example, the actuator 140 illustrated in FIG. 2 takes the form of a simple conical sleeve that is configured to slide or move over, or on the outer surface of the elongated body 102, though it will be apparent that any other form or shape of actuator 140 will suffice. In the retracted position, the actuator 140 is positioned such that its distal end 142 is disposed proximal to the grooves 116a, 116b, of the retention members 120, and the pivotally movable elements 122a and 122b are disposed substantially flush with the lumen wall of the elongated body 102. In the retention position, the actuator 140 may be positioned such that its distal end 142 is disposed distally with respect to the grooves 116a, 116b, of the retention member 120, and the distal ends 124a and 124b of the pivotally movable elements 122a and 122b are disposed within the lumen 104 of the elongated body 102.

The actuator 140 employed to actuate the pivotally movable elements 122a, 122b of the retention member may comprise a manual handpiece, for example, that can be finger/thumb actuated to advance the actuator or sleeve 140 in the distal direction to cause the pivotally movable elements 122a, 122b of the retention member 120 to pivot, and to cause the distal ends 124a, 124b of the pivotally movable elements 122a, 122b respectively, to enter the lumen 104 to coapt or converge. A return spring (not shown) may cause the actuator or sleeve 140 to return to its original position, and to allow the retention member 120 to return to its original retracted position, as previously described. Alternatively, it may be beneficial to incorporate the actuator 140 into a substantially automated, or semi-automated system. Specifically, it could be implemented in a robotically-assisted system, such as those described in the U.S. Publication No. 2007/0106306 already incorporated by reference herein. In this particular embodiment the removal tool 100 may be carried on an automated (e.g., robotic) arm, so that movement of the removal tool relative to the body surface may be performed by either movement of the robotic arm relative to the body surface, or movement of the removal tool relative to the automated arm, or a combination of each. Movement of actuator 140 from a more proximal to a more distal axial location, as necessary to facilitate pivotable movement of the retention member 120 from the retracted to the retention position, may be controlled by the provision of stops (not shown), or by a processor or a controller, or by a computer program, or another such mechanism for restricting such axial movement.

Figure 3:
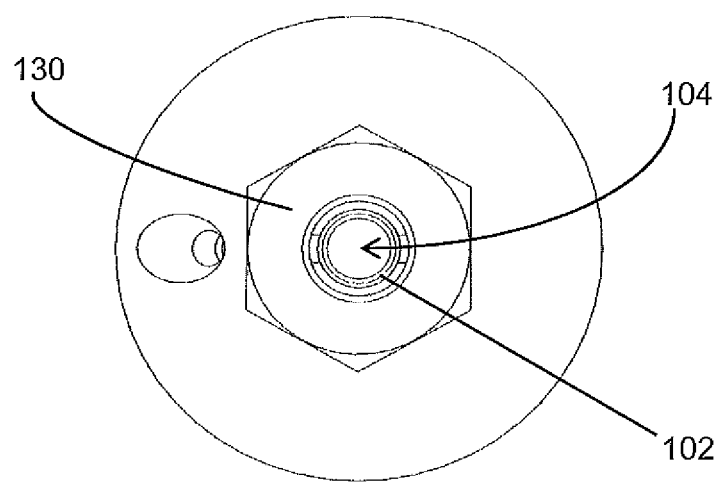
FIG. 3 is an end view of FIG. 2.

FIG. 3 shows the actuator 140 and the pivotable elements 122a and 122b in their retracted positions. The actuator 140 is disposed in a more proximal position, allowing the inner facing surfaces of the distal ends 124a, 124b of the retention member 120 to lie substantially flush with the luminal walls of the elongated body 102, thus enabling the lumen 104 to be substantially clear.

Figure 4A:
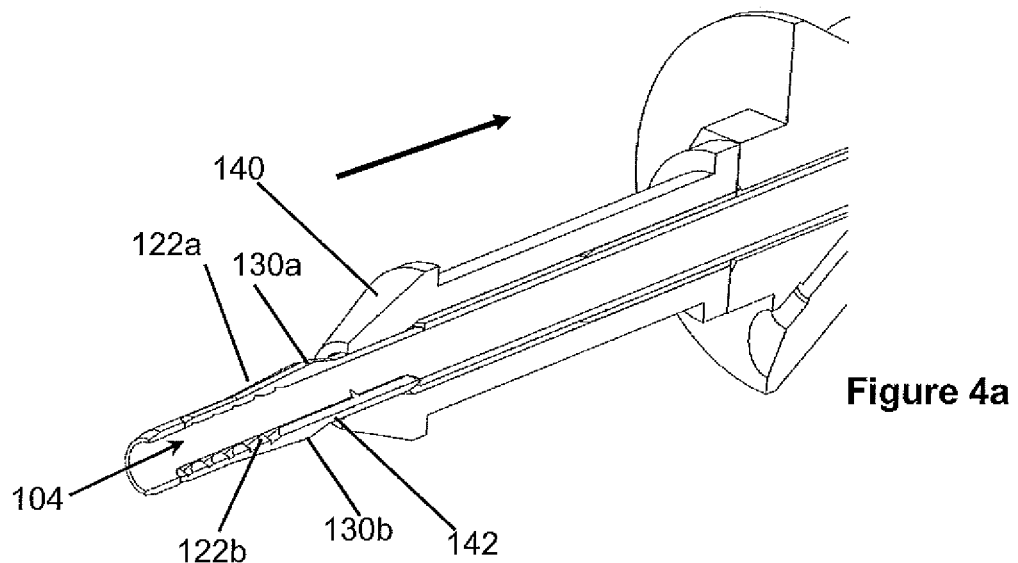
FIG. 4a is a schematic cross-sectional view of an example of a follicular unit removal tool in its retracted position.
Figure 4B:
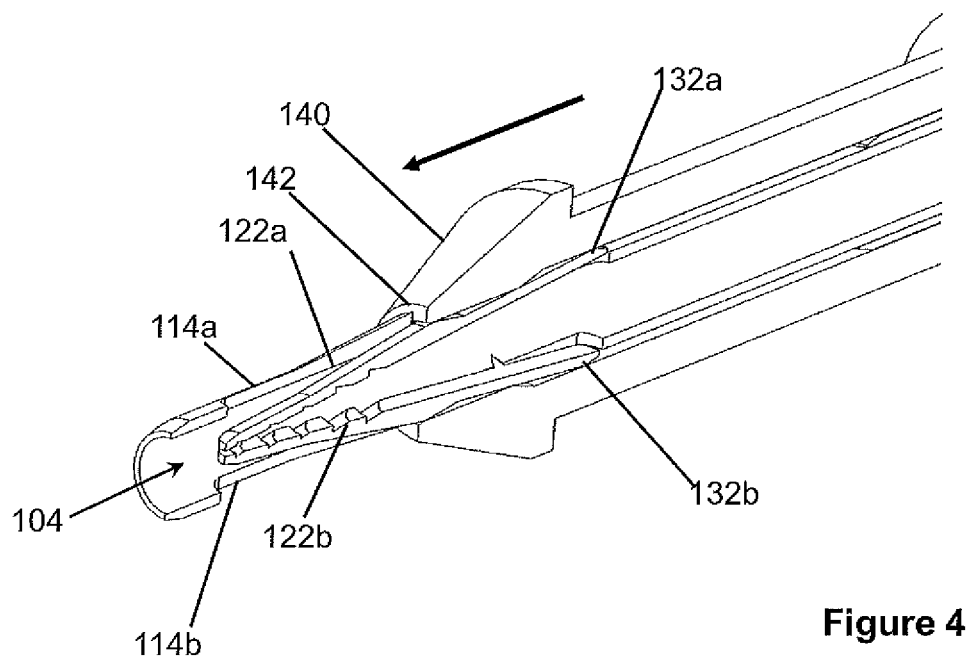
FIG. 4b is a schematic cross-sectional view of an example of a follicular unit removal tool in its retention position.

FIGS. 4a and 4b are cross-sectional views of the retention member 120 in operation, though it should be noted that these figures do not follow conventional standards, as certain areas are not hatched. The deviation from convention serves to aid in clarity of the figures. FIG. 4a shows, as in FIG. 3, the pivotally movable elements 122a and 122b in their retracted positions. Protuberances 130a and 130b may be disposed on the outer surfaces of the pivotably movable elements 122a and 122b. In the retracted position, these protuberances are in an elevated or raised position with respect to the outermost surface of the elongated body 102, while the outer walls of the retention member 120 on either side of the protuberances 130a and 130b lie substantially in-line with, or flush with the outer walls of the elongated body 102. FIG. 4b shows the actuator 140 having been moved in the distal direction (indicated by the arrow), such that the protuberances 130a and 130b (shown in FIG. 4a) are urged radially inwards towards the longitudinal axis of the lumen 104. To aid in this motion, the protuberances may comprise tapered edges such that movement of the actuator 140 in the direction indicated caused the protuberance to slide easily beneath the actuator 140. This movement in the distal direction actuates the pivotally movable elements 122a and 122b such that they pivot about the fulcrums 116a and 116b, and the distal facing portions (the portion distal to the fulcrum) of the pivotally movable elements 122a and 122b pivot towards each other. The proximal ends or portions 132a and 132b of the pivotally movable elements 122a and 122b that lie proximal to the fulcrum 116a, 116b, pivot and move radially outwards away from each other. In this retention position, the proximal portions or ends 132a and 132b of the pivotally movable elements 122a and 122b are shown to protrude slightly from the outer surface of the elongated body 102, but as indicated, can still be confined by the structure of the conical actuator 140.

In the retention position illustrated in FIG. 4b, it can be seen that any follicular unit that was disposed within the lumen 104 of the elongated body 102 would be retained with the inwardly facing surfaces 128a, 128b of the pivotally movable elements 122a and 122b, and its movement impeded in the distal end direction, Contrary to known retention devices, the inclusion of such a retention member 120 in a tool 100 in the manner described enables one to maintain (rather than increase) the external cross-sectional profile or footprint of the tool 100 as it penetrates the body surface, and/or maintain the internal lumen capacity to that of the maximum capacity dictated by the configuration of the internal walls of the tool (rather than compromise to a lesser capacity dictated by the presence of the retention device). Consequently, the inclusion of such a retention member 120 generally does not provide additional "bulk" to the external or internal boundaries of the removal tool 100 in operation, and one is not driven to make certain compromises or sacrifices associated to these external or internal boundaries in order to facilitate the addition of the retention member. As a result, the harvesting or removal tool does not leave a larger wound in the body surface, and also the size of the follicular unit or units that can be removed does not have to be decreased.

Figure 5:
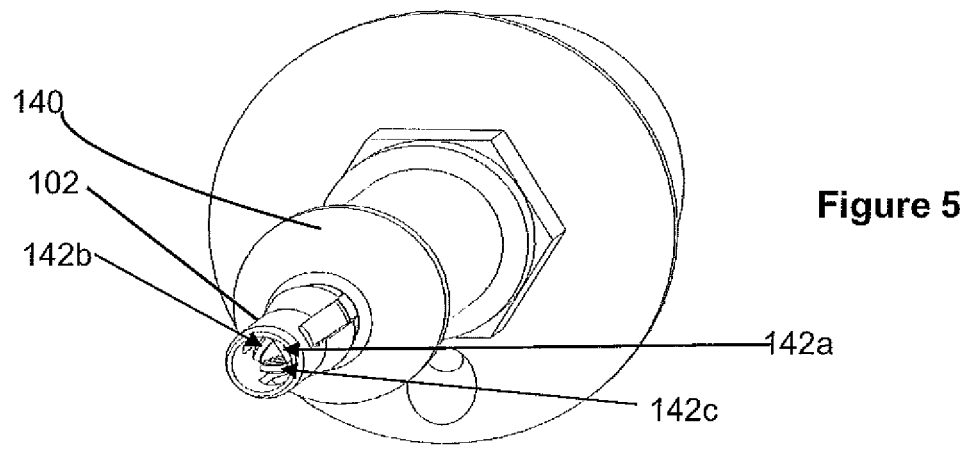
FIG. 5 is an example of a perspective view of a follicular unit removal tool and associated system elements incorporating three pivotable movable elements.

FIG. 5 shows that number of pivotally movable elements of the retention member may be greater than two, in this particular case there are three pivotally movable elements 142a, 142b and 142c. However, as can be seen, movement of the conical actuator 140 is such that all three pivotable movable elements can be substantially simultaneously pivotally moved from their retracted to their retention position by the axial movement of the conical actuator 140 in the distal direction.

In another aspect of the present application, the follicular unit removal tool may comprise two different tubes that are utilized in concert to accomplish harvesting of the hair graft. This tool assembly may include, for example, a pair of coaxially disposed cannulas that are moveable relative to one another. For example, the elongate body 102 that accommodates the retention member, as described, may represent the outer cannula with a blunt distal tip. Such blunt distal tip may be used for dissection of tissue around the follicular unit. The tool assembly may also comprise an inner cannula (not shown) having a relatively sharp distal end, the inner cannula could move axially within the lumen 104 of the elongated body 102. The piercing distal end of the inner cannula may be, for example, thrust through the lumen 104 of the elongated body 102 to pierce the body surface. Then the elongated body 102 may be inserted through the incision created by the inner cannula and into the cutaneous and subcutaneous tissue using blunt dissection, for example, to encapsulate and separate from the surrounding tissue the follicular unit chosen for harvesting. The retention member 120, that is accommodated by the elongated body 102, can then be actuated to pivotally move and retain the follicular unit encapsulated within the lumen 104 of the elongated body 102.

Figure 6:
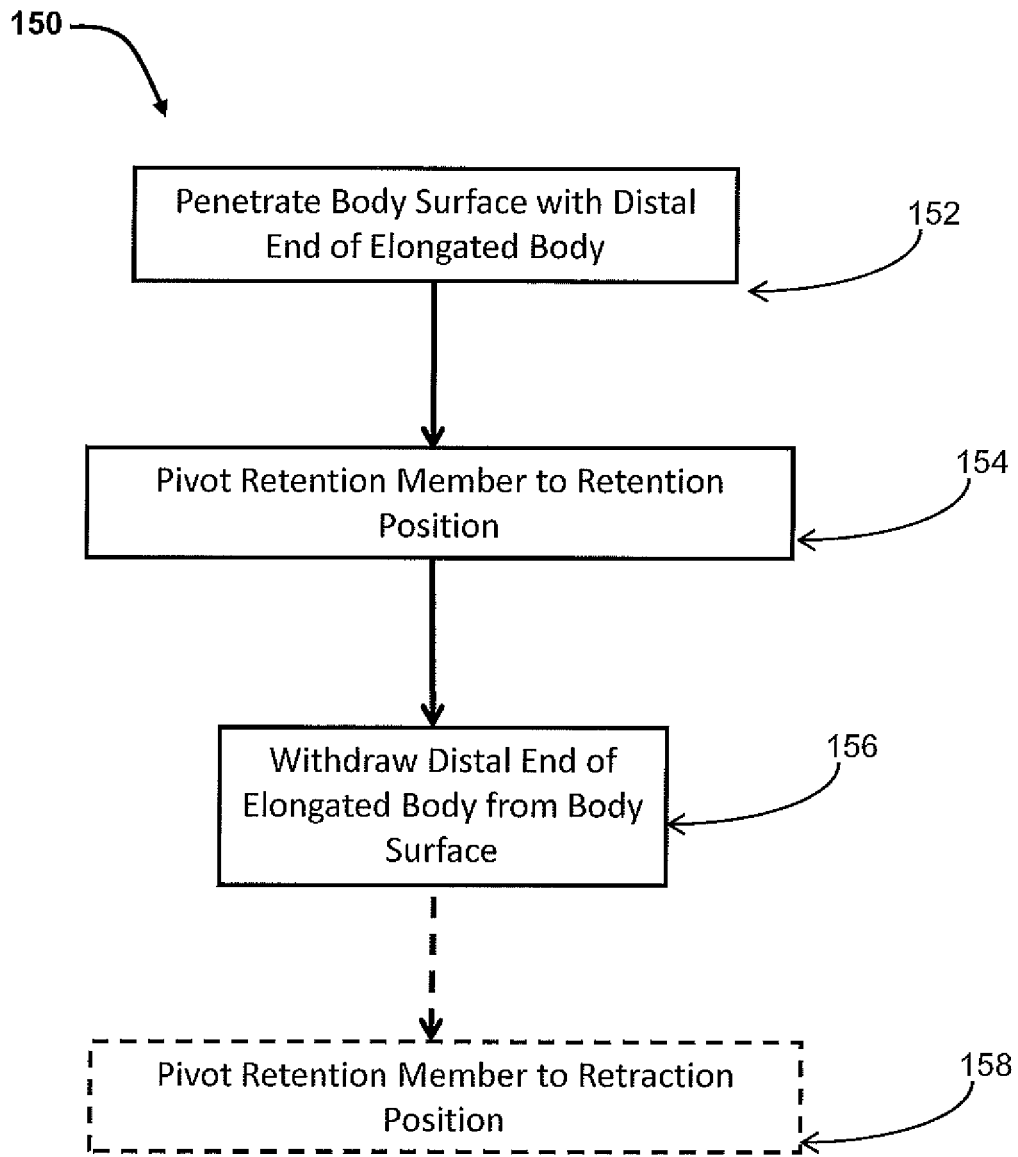
FIG. 6 is a flow diagram of a method of removing a follicular unit according to an embodiment of the present application.

FIG. 6 is a flow diagram of an example of a method 150 that may be practiced using the follicular unit removal tool described above. The user or an operating mechanism (in case of the automated, for example, robotic system), in step 152 moves the removal tool 100 to advance the distal end of the elongated body 102 to penetrate the body surface of a patient with the retention member 120 in its retracted position. The retention member 120 may be placed or configured in its retracted position, for example, before the distal end penetrates the body surface, or while it is penetrating the body surface. This configuration may be carried out simultaneously to the penetration step or as a separate step. To aid in the penetration of the body surface, the removal tool 100 may be rotated or otherwise manipulated to further penetration of the body surface. Once within the body surface, the removal tool is inserted so that its distal end is at the desired insertion depth. While the follicular unit is encapsulated within the lumen 104 of the follicular unit removal tool 100, the retention member is pivoted to the retention position in step 154. Pivotal movement of the retention member 120 from the retracted to the retention position may be caused, for example, by actuating an actuator 140. In some embodiments, as described hereinbefore, this is facilitated by the axial movement of the actuator in a distal direction, for example, to encounter the protrusions 130a, 130b on the pivotally movable elements 122a, 122b, and move the distal ends of the pivotally movable elements 122a, 122b inwards towards the center of the lumen 104 to retain the follicular unit. Once this action has been accomplished, the user (or an operating mechanism) may then withdraw the removal tool 100 (step 156) to remove the follicular unit from the body surface. This step may once again include rotating the removal tool to aid in the severance of the tethered follicular unit from the body surface. Once withdrawn, and removed from the body surface, the removal tool 100 may be optionally reconfigured (e.g., by using the actuator again) such that the retention member 120 is in the retracted position within the elongated body 102, and that the lumen 104 is substantially clear. By doing this, in step 158, the follicular unit can be released from the removal tool and utilized as desired.

In an alternative embodiment, the step 152 of the method discussed above may be modified if, for example, two coaxially disposed cannulas that are moveable relative to one another are used to remove a follicular unit from a body surface. In this embodiment of the method, in step 152 the distal end of an inner cannula (not shown) may be advanced through the lumen 104 of an elongated body 102 to penetrate the body surface of a patient. During this time, it may be preferable to have the retention member 120 in its retracted position within the elongated body 102, so that movement of the inner cannula in the distal direction is not unnecessarily impeded. To aid in the penetration of the body surface, the inner cannula may be rotated or otherwise manipulated to further penetration of the body surface. After initial penetration of the body surface with the distal end of the inner cannula, the elonagated body 102 may be inserted through the incision created by the inner cannula to the desired insertion depth. The inner cannula may be partially or fully withdrawn any time before pivotal movement of the retention member accommodated by the elongated body 102 in step 154. As described in reference to the previous example of the method, the pivotal movement of the retention member may be achieved by actuating an actuator 140. The rest of the method may remain the same as described above.

It will be apparent that the methods described above may be performed manually, or they may be partially or substantially automated, including performed using robotic systems.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While the invention has been described in its preferred embodiments, it is to be understood that the words which have been used are words of description and not of limitation. Therefore, changes may be made within the appended claims without departing from the true scope of the invention. By way of non-limiting example, it will be appreciated by those skilled in the art that particular features or characteristics described in reference to one figure or embodiment may be combined as suitable with features or characteristics described in another figure or embodiment.

What is claimed is:

1. A method for retaining one or more follicular units in a follicular unit removal tool, comprising:
    inserting a follicular unit removal tool comprising an elongated body and a retention member into a body surface, such that a distal end of the elongated body receives one or more follicular units in a lumen of the elongated body; and
    pivoting the retention member as a whole between a retracted position and a retention position about a structure which provides a pivoting axis which is proximal to a distal end of the retention member and distal to a proximal end of the retention member, such that in the retention position at least a portion of the retention member projects into the lumen of the elongated body,
    wherein in the retracted position the retention member defines a portion of the lumen thereof and a size of an outer and an inner cross-sectional profile of a portion of the follicular unit removal tool that comprises the retention member is substantially the same as if the retention member was not present.

2. The method of claim 1, wherein in the retracted position the retention member is at least partially disposed in a wall of the elongated body.

3. The method of claim 1, wherein in the retracted position, an outer surface of the retention member lays substantially along an outer surface of the elongated body.

4. The method of claim 1, wherein pivoting from the retracted to the retention position is carried out without substantially increasing a cross-section of a portion of the follicular unit removal tool that enters the body surface when the tool is in use, and without compromising a capacity of the lumen available to receive the one or more follicular units.

5. The method of claim 1, wherein pivoting the retention member comprises moving an actuator over at least a portion of the elongated body.

6. The method of claim 5, wherein moving the actuator comprises moving the actuator in a distal and/or proximal direction to cause the retention member to pivot.

7. The method of claim 5, wherein the retention member comprises a plurality of pivotable elements and movement of the actuator causes the plurality of pivotable elements to move from the retracted position to the retention position and converge.

8. The method of claim 5, wherein moving the actuator causes a distal end portion of the retention member to move in a direction radially towards a center of the elongated body, and a proximal end portion of the retention member to move in an opposite direction.

9. The method of claim 5, wherein moving the actuator is controlled by one or more stops, manually, by a processor, by a controller, or by a computer program.

10. The method of claim 1, further comprising gripping the follicular unit with a non-traumatic surface of the portion of the retention member that projects into the lumen.

11. The method of claim 1, wherein the step of inserting comprises causing an operating mechanism of a robotic system to insert the follicular unit removal tool into the body surface.

12. The method of claim 1, further comprising connecting the follicular unit removal tool to a source of fluid or gas, to assist movement of the one or more follicular units in the elongated body in a proximal direction.

13. The method of claim 1, wherein the method is substantially automated.

14. A method for retaining one or more follicular units in a follicular unit removal tool, comprising:
    inserting a follicular unit removal tool comprising an elongated body and a retention member into a body surface, such that a distal end of the elongated body receives one or more follicular units in a lumen of the elongated body; and
    pivoting the retention member between a retracted position in which a proximal end and a distal end of the retention member are substantially flush with the lumen of the elongated body such that the retention member defines a portion of the lumen and a retention position in which as the proximal end of the retention member is urged outward in a radial direction, the distal end of the retention member is urged radially inward in an opposite direction into the retention position where at least a portion of the retention member projects into the lumen of the elongated body.

15. The method of claim 14, further comprising moving an actuator in a distal and/or proximal direction to cause the retention member to pivot.

16. The method of claim 15, wherein the retention member comprises a plurality of pivotable elements and moving the actuator causes the plurality of pivotable elements to move from the retracted position to the retention position and converge.

17. The method of claim 14, wherein, when pivoted into the retracted position, the retention member is configured without substantially increasing a cross-section of a portion of the follicular unit removal tool that is inserted into the body surface, and without compromising the capacity of the lumen available to receive the one or more follicular units.

18. The method of claim 14, wherein pivoting the retention member between the retracted position and the retention position comprises moving the distal end of the retention member through a side opening of the elongated body.

19. The method of claim 14, further comprising gripping the follicular unit with the portion of the retention member that projects into the lumen.

20. The method of claim 14, further comprising withdrawing the removal tool to remove the follicular unit from the body surface and reconfiguring the retention member to the retracted position within the elongated body to keep the lumen substantially clear.

21. The method of claim 14, wherein pivoting the retention member comprises pivoting about a pivoting axis disposed proximally to the distal end of the retention member and distally to the proximal end of the retention member.

22. The method of claim 21, wherein the pivoting axis comprises a pivoting structure disposed in a surface of the elongated body.

23. The method of claim 14, wherein in the retracted position the retention member is at least partially disposed in a wall of the elongated body.

24. The method of claim 14, further comprising urging a protuberance disposed away from an end of the retention member towards the lumen of the elongated body such that the retention member pivots.

25. The method of claim 14, wherein the step of inserting comprises causing an operating mechanism of a robotic system to insert the follicular unit removal tool into the body surface.

* * * * *